United States Patent [19]

Johnson et al.

[11] 4,224,943

[45] Sep. 30, 1980

[54] CANNULA AND METHOD FOR BIDIRECTIONAL BLOOD FLOW

[75] Inventors: Robert H. Johnson, Sandy; Dixon A. Ford, Farmington; Gordon S. Reynolds, Bountiful; James L. Sorenson, Salt Lake City, all of Utah

[73] Assignee: Sorenson Research Co., Inc., Salt Lake City, Utah

[21] Appl. No.: 6,053

[22] Filed: Jan. 24, 1979

Related U.S. Application Data

[63] Continuation-in-part of Ser. No. 821,848, Aug. 4, 1977, abandoned.

[51] Int. Cl.³ ............................................... A61M 5/00
[52] U.S. Cl. ................................. 128/214.4; 128/221; 128/DIG. 16
[58] Field of Search .................... 128/214.4, 221, 347, 128/348, DIG. 16

[56] References Cited

U.S. PATENT DOCUMENTS

| | | | |
|---|---|---|---|
| 2,688,329 | 9/1954 | Wallace | 128/349 R |
| 3,185,152 | 5/1965 | Ring | 128/214.4 |
| 3,262,449 | 7/1966 | Pannier et al. | 128/214.4 |
| 3,297,030 | 1/1967 | Czorny et al. | 128/214.4 |
| 3,406,685 | 10/1968 | May | 128/214.4 |
| 3,459,183 | 8/1969 | Ring et al. | 128/214.4 |
| 3,463,152 | 8/1969 | Sorenson | 128/214.4 |
| 3,474,786 | 10/1969 | Spademan | 128/214.4 |
| 3,537,453 | 11/1970 | Drummond et al. | 128/218 C |
| 3,547,119 | 12/1970 | Hall et al. | 128/214.4 |
| 3,572,334 | 3/1971 | Petterson | 128/214.4 |
| 3,584,624 | 6/1971 | De Ciutiis | 128/214.4 |
| 3,610,226 | 10/1971 | Albisser | 128/214 R X |
| 3,726,269 | 4/1973 | Webster | 128/348 X |
| 3,739,778 | 6/1973 | Monestere et al. | 128/214.4 |
| 3,766,916 | 10/1973 | Moorehead et al. | 128/214.4 |
| 4,037,600 | 7/1977 | Poncy et al. | 128/214.4 |
| 4,073,297 | 2/1978 | Kopp | 128/214.4 |
| 4,079,738 | 3/1978 | Dunn et al. | 128/214.4 |
| 4,096,860 | 6/1978 | McLaughlin | 128/214.4 |
| 4,099,528 | 7/1978 | Sorenson et al. | 128/214.4 |
| 4,149,535 | 4/1979 | Volder | 128/214.4 |

OTHER PUBLICATIONS

Kruger-IBM Tech. Disclosure Bulletin, vol. 19, No. 4, Sep. 1976.

*Primary Examiner*—Dalton L. Truluck
*Attorney, Agent, or Firm*—H. Ross Workman; J. Winslow Young; Rick D. Nydegger

[57] ABSTRACT

A cannula and method for bidirectional blood flow, the cannula being constructed so as to provide a bifurcated flow path, each branch of the flow path independently communicating through telescoping cannulae and a venipuncture needle initially projecting beyond the exterior cannula to facilitate venipuncture and thereafter being displaceable away from the venipuncture site to permit unobstructed simultaneous fluid flow in opposite directions through each of the bifurcated flow paths.

10 Claims, 4 Drawing Figures

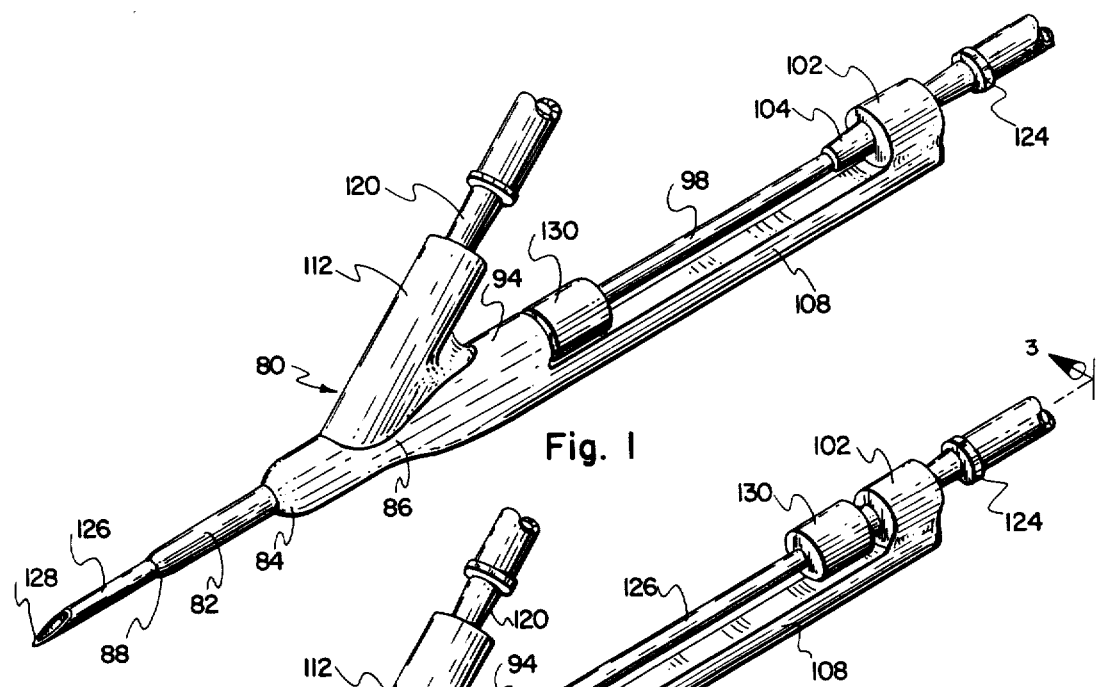
Fig. 1
Fig. 2
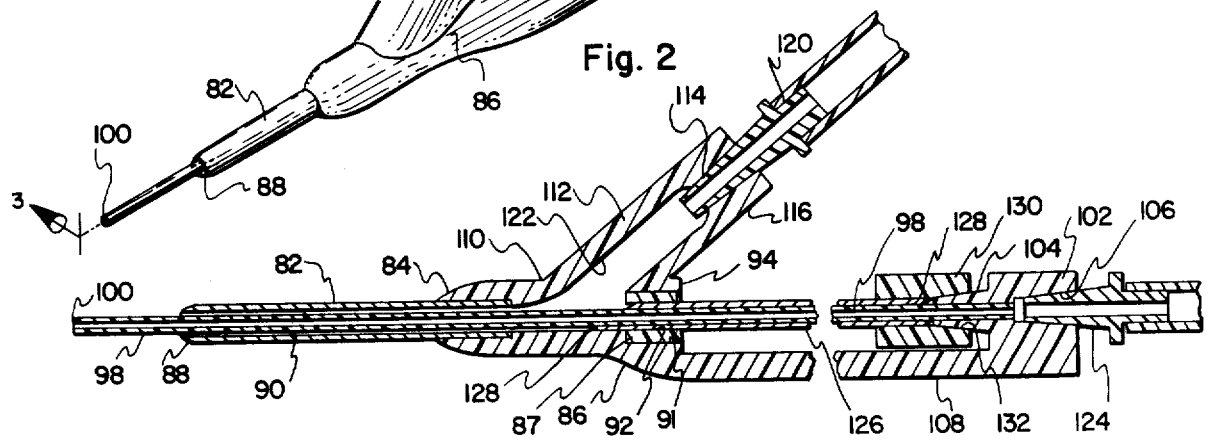
Fig. 3
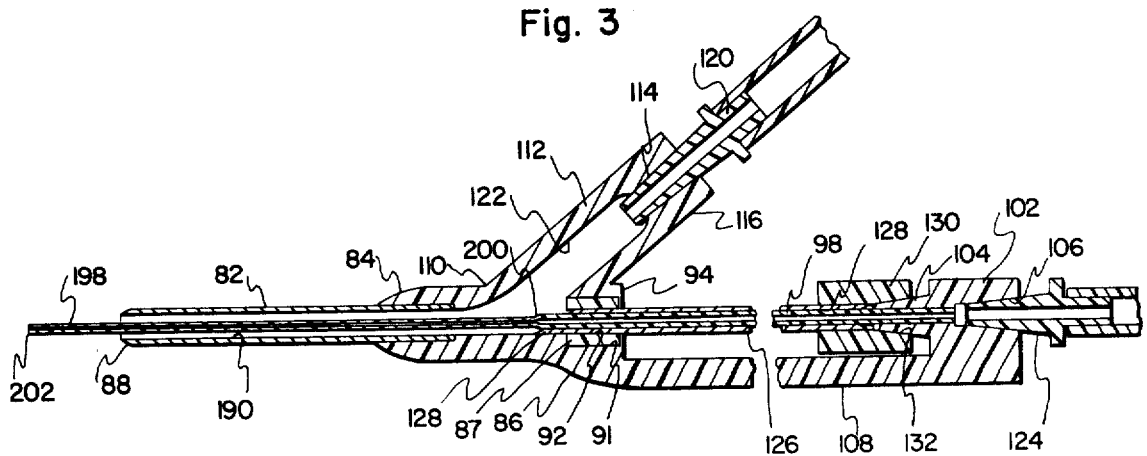
Fig. 4

CANNULA AND METHOD FOR BIDIRECTIONAL BLOOD FLOW

BACKGROUND

RELATED APPLICATION

This application is a continuation-in-part of my copending U.S. patent application Ser. No. 821,848, filed Aug. 4, 1977, now abandoned.

FIELD OF THE INVENTION

The present invention relates to a cannula for medical use and more particularly to a double lumen cannula for independently conducting fluids into and out of a venipuncture site through two separate passageways.

THE PRIOR ART

Double lumen cannulae are well known in the art. The best known advantage offered by double lumen cannulae is the ability to separately withdraw blood from a blood vessel and inject blood back into the same blood vessel through a single venipuncture or fistula. The most common double lumen cannulae consist of a single tube with a horizontal division of the tube which places the lumen of the cannulae in immediate juxtaposition. Unfortunately, however, the construction of such double lumen cannulae is expensive, time consuming and unreliable.

The least expensive and most reliable construction of the double lumen cannulae is in the form of concentric lumen disposed telescopically one within the other. Particularly when using cannulae for single needle dialysis, it is preferred to have one cannula lumen project substantially beyond the other. Attention is directed particularly to the common use of cannulae for single needle dialysis such as that disclosed and described in U.S. Pat. No. 3,756,234. In single needle dialysis, it is highly desirable to withdraw blood from a patient, treat the blood with a hemodialyzer (artificial kidney) and return the blood to the patient through the same fistula in which the blood was withdrawn. Under such circumstances, it is desirable to return the blood a significant distance upstream from where the blood is aspirated so as to minimize the problem of admixing.

The problems with such telescopic construction are apparent when it is observed that both cannula must be used to penetrate the skin during venipuncture. Unless there is a smooth contour between the interior and exterior cannula, the venipuncture is both difficult and painful. On the other hand, if the telescoping cannulae present an exteriorly smooth surface for venipuncture, there is insufficient passageway for fluid to flow easily between the lumen. The structure of a double lumen cannula lends itself admirably to the ability to aspirate blood from a downstream location and to return blood at an upstream location all through the same fistula. However, until this present invention, structure and method for introducing a double lumen cannula into the bloodstream and for maintaining separate flow paths through a single fistula has not been known.

BRIEF SUMMARY AND OBJECTS OF THE INVENTION

The present invention, including method and apparatus, provides bifurcated flow paths through coextensive cannulae, the cannulae being introduced into the blood vessel initially by a needle which is thereafter removed to facilitate unobstructed flow through the independent flow paths established at a single fistula.

It is, therefore, a primary object of the present invention to provide an improved double lumen cannula.

It is another primary object of the present invention to provide a method of aspirating blood and returning blood through separate flow paths and through a single fistula.

It is another primary object of the present invention to provide a novel double lumen cannula and method in which the needle is removed from the puncture site after venipuncture without adversely interfering with the blood flow paths.

Another important object of the present invention is the provision for an elongated diametrally reduced portion of the inner cannula lumen over a predetermined portion of its length to provide for maximum flow between the lumen at minimum resistance.

These and other objects and features of the present invention will become more fully apparent from the following description and appended claims taken in conjunction with the accompanying drawing.

BRIEF DESCRIPTION OF THE DRAWING

FIG. 1 is a perspective illustration of a presently preferred cannula embodiment with a reciprocating needle, the needle being illustrated in the forward most, initial position.

FIG. 2 is a perspective illustration of the embodiment of FIG. 1 with the needle in the retracted position.

FIG. 3 is a cross section taken along lines 3—3 of FIG. 2.

FIG. 4 is a cross-sectional view of another preferred embodiment of the present invention particularly illustrating a lumen configuration for minimizing the resistance.

DETAILED DESCRIPTION OF THE PREFERRED EMBODIMENTS

Attention is now directed to the figures wherein like parts are designated with like numerals throughout.

One presently preferred cannula assembly embodiment generally designated 80 is illustrated best in FIGS. 1-3. The duplex cannula illustrated in FIGS. 1-4 is intended to be used in any medical service and which bidirectional blood flow through a single fistula is desirable. One such medical service includes the creation of a single fistula for blood hemodialysis. In the description which follows, it will become apparent that the single fistula created by proper insertion of the duplex cannula 80 will permit blood to be withdrawn from and returned to a patient without creating an additional fistula and without otherwise modifying the structure of the assembly 80. The withdrawal and return of blood may occur simultaneously or serially, as desired. Moreover, the needle which is used to create the fistula through the surface of the skin can be easily and safely withdrawn from the fistula and concealed safely within the needle hub so as to prevent injury to patient or to the catheter without any auxiliary structure or needle protection devices.

More particularly, the assembly 80 comprises an exterior cannula 82 which is mounted at the forward end 84 of a cannula hub 86. Preferably, the exterior cannula 82 is forwardly tapered at 88 and defines an interior bore 90 (see FIG. 3). The bore 90 of the cannula 82 communicates directly with a recess 91 in the hub 86. The recess 91 opens at the trailing end 94 of the hub 86.

Rubber sleeve 87 is nested within recess 91 and defines a throughbore 92 which tightly circumscribes needle 126 to form an air-tight seal as will hereinafter be more fully described.

An interior catheter or cannula 98 traverses the entire throughbore 92 and the bore 90 of exterior cannula 82. The leading end 100 of the catheter 98 projects beyond the leading end 88 of cannula 82 as shown in both FIGS. 2 and 3. The trailing end of catheter 98 is mounted within coupling member 102, the coupling member 102 having a male Luer fitting 104 which is in direct alignment with the throughbore 92. The interior catheter 98 is hollow and opens directly into the female Luer coupling 106. The coupling member 102 is maintained in direct alignment and fixed axial spacial relationship with the hub 86 by a strut 108. It can be seen, therefore, that there is a discrete passageway from the leading tip 100 of the catheter 98 through the entire length of the catheter 98 to the coupling member 102.

The cannula hub 86 is bifurcated at 110 to form a branch 112. The branch 112 has a female Luer fitting 114 at its trailing end 116 into which a suitable coupling 120 from a conventional extracorporeal fluid circuit is press-fit. The branch 112 has a hollow interior 122 which communicates directly with the bore 90 of exterior cannula 82. Accordingly, a discrete passageway exists through the bore 90 and hollow 122 to the coupling 120. In addition, a separate and discrete passageway exists through the hollow of interior catheter 98 to the trailing end of coupling member 102 and to a male coupling 124 press-fit therein. Significantly, the structure of the cannula assembly 80 permits the extracorporeal fluid circuit at 120 and 124 to be attached prior to venipuncture and to remain attached during and after venipuncture. Thus, the assembly 80 can be flushed with sterile fluid and introduced into the patient without break in sterile technique.

In order to facilitate introduction of the coextensive cannulae 82 and 98, a venipuncture needle 126 is provided. The venipuncture needle 126 has a sharp beveled end 128 which, in the initial position illustrated in FIG. 1, projects through the interior of cannula 82 and telescopically around and beyond catheter 98. With reference to FIG. 3, it can be appreciated that the needle 126 is reciprocably displaceable within the bore 92 of the sleeve 87. The sleeve 87 forms an air-tight seal with needle 126 so that negative pressure within the hub 86 and branch 112 will not draw air around the needle 126 into the blood within the hub. The trailing end 128 of the needle 126 is firmly mounted to a shuttle 130, the shuttle having a rearwardly facing female fitting 132 which is selectively press-fit upon the male fitting 104 of the coupling member 102 as illustrated in FIG. 3. Clearly, the location of the male fitting 104 and female fitting 132 could be reversed without adverse consequence. This press-fit coupling minimizes blood leakage around the needle 126 after venipuncture and forms an air seal for preventing air from entering the hub 86 when the interior of hub 86 is subjected to negative internal pressure.

The method of using the embodiment of FIGS. 1-3 is apparent from the drawing. Initially, the shuttle 130 is advanced forwardly until the needle 126 projects beyond the leading end 88 of the cannula 82 and substantially circumscribes and confines the interior catheter 98. By restraining the shuttle 130 in place with the fingers, the venipuncture can easily be made. It is observed, however, that the needle 126 will substantially fill the passageway in the throughbore 90 between the cannula 82 and the catheter 98. Accordingly, blood will not flow through the bore 90 and hollow 122 in the branch 112 while the needle is in the forward position illustrated in FIG. 1.

After venipuncture has been successfully accomplished and the fistula established, the shuttle 130 may be manually displaced rearwardly and telescopically over the exposed portion of the interior catheter 98 until the shuttle 130 mates with the coupling member 102. In this mode, blood will freely flow between the cannulae 82 and 98, through the branch 112 and the extracorporeal blood circuit connected at 120. At the same time, blood may also flow through the hollow of the interior catheter 98 along the discrete flow path defined by the interior catheter 98 and through the coupling 124 to the extracorporeal fluid circuit. As described above, the assembly 80 may be coupled to the extracorporeal fluid circuit before venipuncture, if desired. Prior coupling may facilitate flushing of the assembly with sterile fluid for subsequent blood aspiration or fluid delivery into the blood stream.

The length of the needle 126 and the strut 108 are selected so that when the shuttle 130 is in the rearmost position illustrated in FIGS. 2 and 3, the sharpened leading end 128 of the needle 126 will remain supported and protected by the cannula hub 86 but be fully retracted out of the pathway 122 so as to avoid interfering with the blood flow. In this retracted position, the needle is safely preserved to avoid injury to patient or catheter. Clearly, the needle can be reciprocated without disconnection of the assembly 80 from the extracorporeal fluid circuit.

Reference is now directed to the embodiment of FIG. 4 which differs from the embodiment of FIGS. 1-3 only in the structure of the interior catheter 198. The interior catheter 198 is diametrally reduced in both inside and outside diameter from the intermediate point 200 to the proximal end 202 of catheter 198.

It has been well known for a number of years to slightly taper the proximal end of a catheter to facilitate insertion of the catheter into a blood vessel. The taper facilitating this purpose is illustrated at the proximal end 88 of the exterior catheter 82 illustrated in FIGS. 1 and 2. Clearly, an exterior taper to facilitate insertion is not necessary for the catheter 198 because catheter 198 is typically surrounded by the needle 126 prior to venipuncture (see, for example, FIG. 1).

In the embodiment of FIG. 4, it is contemplated that blood will be transferred from a high pressure system to the patient through the catheter 198. Conversely, blood will be withdrawn from the patient through the catheter 82 and the space 190 between the catheter 82 and the catheter 198 into the patient through the branch 112. Because the blood displaced through the space 190 and the branch 112 is transported due to negative pressure caused by a blood pump or other suitable negative pressure producing device, resistance to flow in the space 190 is of critical importance. Accordingly, the interior catheter 198 has been reduced in inside and outside dimension so as to create a reduced resistance to flow in the space 190 between the leading end 88 of the cannula 82 and the sleeve 87 located at the trailing end of the branch 112. On the other hand, if the entire catheter 198 were reduced in dimension, it has been found that the pressure necessary to force the blood into the patient through the lumen of interior catheter 198 is too great.

Accordingly, catheter 198 has an increased dimension at the proximal end beginning at the point 200.

By way of example only, it has been found desirable to have the largest diametral dimensions of catheter 198 at about 0.57 inches ID and 0.61 inches OD. The reduced dimension for catheter 198 may desirably be on the order of 0.66 inches ID and 0.71 inches OD.

The aforedescribed catheter with an intermediately reduced dimension has been found surprisingly effective in permitting blood to flow easily through the space 190 responsive to the negative pressure transmitted through branch 112 and at the same time avoid the serious effects of materially increasing the pressure with which the blood would be forced to endure if the smallest dimension of catheter 198 extended the entire length thereof into the coupling member 102.

Clearly, in the embodiments illustrated herein structure and method have been described which facilitates successful cannulation of a blood vessel and, after cannulation, the displacement and/or removal of the sharpened needle to permit essentially simultaneous aspiration of blood from the patient and delivery of blood back to the patient through two discrete flow paths in the assembly.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cannula assembly comprising in combination:
   a bifurcated cannula hub and a first hollow cannula mounted in the hub at a first location so as to communicate with one branch of the bifurcated hub;
   a second hollow cannula essentially coextensible with the first cannula and mounted in the hub at a second location so as to communicate with the other branch of the bifurcated hub, the second location being spaced from the first along the axis of the cannula;
   means defining a first flow path between the first cannula and the corresponding one branch of the hub and means defining a second flow path between the second cannula and the corresponding other branch of the hub, the first and second flow paths being attachable to extracorporeal fluid lines and being separated one from the other;
   a hollow venipuncture needle telescopically disposed within the first cannula and around said second cannula and projecting therebeyond to facilitate introduction of both the first and second cannulae into a blood vessel; and
   means for displacing the venipuncture needle away from the blood vessel after cannulation thereof such that at least a portion of the needle is permanently retained within the assembly, said displacing means accommodating venipuncture without interferring with the communication of the flow paths to the extracorporeal fluid lines, thereby facilitating essentially simultaneous exposure of both the first and second cannulae to blood within the vessel.

2. A cannula assembly as defined in claim 1 wherein said displacing means comprises a shuttle member mounted upon the trailing end of the needle and displaceable reciprocably between a forward position which exposes the needle beyond the distal end of the cannulae and a retracted position which confines the sharp end of the needle safely within the hub and simultaneously leaves the flow path means unobstructed by the needle.

3. A cannula assembly as defind in claim 2 wherein said retracted position is defined by a coupling member axially aligned with the rigid hub and secured thereto a spaced distance from the trailing end of the hub, the member presenting a forwardly projecting male coupling onto which the reciprocating member is securable, the male coupling interiorly defining a flow path which is in open communication with the hollow of the interior cannula.

4. A cannula assembly as defined in claim 1 wherein said second hollow cannula is diametrally reduced in inside and outside dimension through an axial portion of its length which corresponds at least to the length of the first hollow cannula.

5. A cannula assembly comprising in combination:
   a bifurcated cannula hub;
   a first hollow cannula mounted upon the leading end of the bifurcated cannula hub and projecting forwardly thereof a first distance;
   a second hollow cannula telescopically disposed within the first, the leading end of the second cannula projecting beyond the leading end of the first cannula and the trailing end of the second cannula being attached to a spaced rigid coupling member so as to be in direct axial alignment with one branch of the bifurcated cannula hub;
   means for fixing the position of the spaced coupling with respect to the rigid hub;
   the second branch of the bifurcated coupling defining a hollow flow path which flow path intersects the interior of the first hollow cannula within the rigid hub;
   a venipuncture needle, the trailing end of which is secured to a reciprocating shuttle member, the leading end of the needle being reciprocably disposed within the rigid cannula hub and telescopically circumscribing the second cannula; and
   means accommodating displacement of the needle and shuttle from a first position in which the shuttle is in a forward position adjacent the rigid cannula hub and the needle is interposed between the first and second cannulae and projecting forward of the first cannula so as to accommodate venipuncture and a second position wherein the shuttle is rearwardly displaced into engagement with the spaced coupling thereby withdrawing the needle from within the first cannula and removing its obstructing presence from the intersecting flow path whereby blood can be simultaneously conveyed in one direction through the first hollow cannula and in the opposite direction through the second hollow cannula.

6. A cannula assembly as defined in claim 5 further comprising means forming an air-seal between the needle and the cannula hub to minimize air influx into the hub when the hub is subjected to negative pressure.

7. A cannula assembly comprising in combination:
   a bifurcated cannula hub, a first hollow cannula mounted within the cannula hub, a second hollow cannula likewise mounted within the cannula hub in telescopic relation within the first hollow cannula and a needle superimposed over the second cannula and telescopically disposed within the first cannula, said needle reciprocating from a forward position in which the sharpened leading end of the needle is exposed beyond the first hollow cannula to a second position in which the leading end is retracted out of the first hollow cannula, said second hollow cannula having a diametrally reduced portion through that portion of its length which is telescopically circumscribed by the first hollow cannula.

8. A method of introducing a double lumen cannula into the cardiovascular system of a patient, the double lumen cannula comprising a branched hub with a first and second cannula, each of said cannulae being interiorly hollow, the method comprising the steps of:
connecting one branch of the cannula hub to an extracorporeal fluid circuit and connecting another branch of the cannula to the extracorporeal fluid circuit;
interposing a stylet needle through the hollow of a first cannula, the stylet needle being interiorily hollow and having a trailing end mounted in a shuttle member;
initially concealing a second smaller diameter cannula telescopically within the hollow of the stylet needle;
simultaneously introducing both the first and second cannulae into the cardiovascular system of a patient without disconnecting the cannula hub from the extracorporeal blood circuit; and
displacing the stylet needle away from the leading ends of the first and second cannulae and within the cannula hub by grasping the shuttle member and displacing the shuttle member a limited distance along the axis of the second cannula.

9. A double lumen cannula assembly for use in a cardiovascular system of a patient comprising in combination:
a hollow hub;
a first lumen mounted in the hub to define a flow path to a first extracorporeal line;
a second lumen mounted in the hub to define a flow path to a second extracorporeal fluid line, a portion of said second lumen being essentially coextensible within the distal end of the first lumen;
a needle telescopically disposed within the first lumen and projecting therebeyond, said needle being disposed around the second lumen so as to facilitate essentially concurrent introduction of the first and second lumens into the cardiovascular system; and
means for retracting the needle a limited distance along the axis of the second lumen away from said distal end such that the sharp end of the needle is retained in the hub, said displacing means accommodating venipuncture without interrupting communication of the flow paths of the first and second lumen to the respective extracorporeal fluid lines.

10. A double lumen cannula assembly as defined in claim 9 wherein said retracting means comprises a shuttle member mounted upon the trailing end of the needle and reciprocably displaceable between a forward position which exposes the needle beyond the distal end of the lumen and a retracted position which confines the sharp end of the needle safely within the hub and simultaneously leaves the flow paths of the lumens unobstructed by the needle.

* * * * *